United States Patent
Moya et al.

(10) Patent No.: US 9,415,353 B2
(45) Date of Patent: Aug. 16, 2016

(54) ULTRAFILTRATION MEMBRANES AND METHODS OF MAKING AND USE OF ULTRAFILTRATION MEMBRANES

(75) Inventors: Wilson Moya, Concord, MA (US); Mikhail Kozlov, Belmont, MA (US)

(73) Assignee: EMD Millipore Corporation, Billerica, MA (US)

( * ) Notice: Subject to any disclaimer, the term of this patent is extended or adjusted under 35 U.S.C. 154(b) by 1664 days.

(21) Appl. No.: 12/658,980

(22) Filed: Feb. 18, 2010

(65) Prior Publication Data

US 2010/0159143 A1 Jun. 24, 2010

Related U.S. Application Data

(62) Division of application No. 11/542,834, filed on Oct. 4, 2006.

(60) Provisional application No. 60/726,745, filed on Oct. 14, 2005.

(51) Int. Cl.
*B01D 71/68* (2006.01)
*B01D 67/00* (2006.01)
*A61L 2/00* (2006.01)
*B01D 69/02* (2006.01)
*B01D 69/10* (2006.01)

(52) U.S. Cl.
CPC .............. *B01D 71/68* (2013.01); *A61L 2/0017* (2013.01); *B01D 67/0083* (2013.01); *B01D 67/0088* (2013.01); *B01D 67/0093* (2013.01); *B01D 69/02* (2013.01); *B01D 69/10* (2013.01); *B01D 2323/02* (2013.01); *B01D 2325/20* (2013.01); *B01D 2325/36* (2013.01)

(58) Field of Classification Search
None
See application file for complete search history.

(56) References Cited

U.S. PATENT DOCUMENTS

| 4,413,074 | A | 11/1983 | Wrasidlo et al. |
| 4,794,002 | A | 12/1988 | Henis et al. |
| 5,139,881 | A | 8/1992 | Henis et al. |
| 5,698,281 | A * | 12/1997 | Bellantoni et al. ........... 428/35.7 |
| 5,919,370 | A | 7/1999 | Rottger et al. |
| 6,214,382 | B1 | 4/2001 | Eguchi et al. |
| 6,579,342 | B2 | 6/2003 | Wang et al. |
| 6,770,202 | B1 | 8/2004 | Kidd et al. |
| 2003/0217965 | A1 | 11/2003 | Kools |
| 2007/0084788 | A1 | 4/2007 | Moya et al. |
| 2008/0004205 | A1 | 1/2008 | Tkacik et al. |
| 2009/0176052 | A1 * | 7/2009 | Childs ................ B01D 67/0009 428/101 |

FOREIGN PATENT DOCUMENTS

| CA | 819509 | 8/1969 |
| EP | 0257635 | 3/1988 |
| EP | 1121972 | 8/2001 |
| WO | WO2004/056460 | 7/2001 |

OTHER PUBLICATIONS

Chapter 19: Membrqane Filtration (date unknown) <<http://www.mrwa.com/Chapter19MembraneFiltration.pdf>>.*
European Search Report EP1775016, Feb. 16, 2007.

* cited by examiner

*Primary Examiner* — Krishnan S Menon
(74) *Attorney, Agent, or Firm* — Hamilton, Brooks, Smith & Reynolds, P.C.

(57) ABSTRACT

An inherently hydrophobic polymer membrane substrate having its surface rendered hydrophilic with a hydroxyalkyl cellulose and having a throughput greater than about 1500 $L/m^2$ is provided. A process for making the membrane also is provided which includes a step of autoclaving in boiling water and/or steam or submerging in boiling water. The membrane is useful for removing virus from a protein solution.

21 Claims, No Drawings

ULTRAFILTRATION MEMBRANES AND METHODS OF MAKING AND USE OF ULTRAFILTRATION MEMBRANES

CROSS REFERENCE TO RELATED APPLICATION

The present patent application is a Divisional patent application of U.S. patent application Ser. No. 11/542,834, filed Oct. 4, 2006, which claims the benefit of priority of U.S. Provisional Patent Application No. 60/726,745, filed on Oct. 14, 2005, each of which are hereby incorporated by reference in their entirety.

FIELD OF INVENTION

This invention relates to membranes having at least one ultrafiltration layer, to a novel method of manufacturing such membranes and to the use of the membranes. More particularly, this invention relates to ultrafiltration membranes having a modified hydrophilic surface, their method of making and their use to remove viruses from a biomolecular solution.

BACKGROUND

Ultrafiltration and microporous membranes are used in pressure-driven filtration processes. Practitioners in the field of separation processes by membranes easily differentiate between microporous and ultrafiltration membranes and generally distinguish between them based on their application and aspects of their structure. Microporous and ultrafiltration membranes are made, sold and used as separate and distinct products. Despite some overlap in nomenclature, they are separate entities, and are treated as such in the commercial world.

Ultrafiltration membranes are primarily used to concentrate or diafilter soluble macromolecules such as proteins, DNA, viruses, starches and natural or synthetic polymers. In the majority of uses, ultrafiltration is accomplished in the tangential flow filtration (TFF) mode, where the feed liquid is passed across the membrane surface and those molecules smaller than the pore size of the membrane pass through (filtrate) and the remaining molecules (retentate) are retained on the first side (upstream) of the membrane. As fluid also passes through there is a need to recycle or add to the retentate flow in order to maintain an efficient TFF operation. One advantage of using a TFF approach is that as the fluid constantly sweeps across the face of the membrane it tends to reduce fouling and polarization of the solutes at and near the membrane surface leading to longer life of the membrane. Ultrafiltration membranes also can be utilized in dead end filtration mode. Dead-end filtration refers to filtration where the entire fluid stream being filtered passes through the filter with no recycle or retentate flow. Whatever material doesn't pass through the filter is left on its upper (upstream) surface.

Microporous membranes are primarily used to remove particles, such as solids, bacteria, and gels, from a liquid or gas stream in dead-end filtration mode.

Ultrafiltration membranes are generally skinned asymmetric membranes, made for the most part on a support which remains a permanent part of the membrane structure. The support can be a non-woven or woven fabric, or a preformed membrane. Alternatively, a supported ultrafiltration membrane can be formed by cocasting two or more polymer solutions followed by coagulating the solution to form a multi-layer membrane wherein at least one layer is an ultrafiltration membrane.

Viral removal membrane filters are increasingly being used in the biotechnology industry to provide for the safety of the therapeutic products being manufactured. These filters must remove a high proportion of any viruses that may be present while allowing most if not all of the product protein to pass through the membrane. Additionally, it is necessary that the filtration not be prematurely stopped or slowed to a uneconomically low rate of flow by plugging of the porous filter. Practitioners in the field of membrane development have found that to develop a membrane product with this desired combination of properties is indeed a challenge.

In the prior art, viral removal membranes are typically ultrafiltration membranes made to be hydrophilic and low protein binding by polymerizing a crosslinked polymeric coating on the inner porous surface and facial surfaces of the membrane. Without being limited by the following explanation, it is believed such coating processes give a randomly distributed coating thickness on the surfaces of the pores, due to the distribution of pore sizes and the stochastic nature of free radical polymerization. Since the tolerances required for an improved viral removal membrane are very strict, a method of more closely controlling coating thickness was sought.

When filtering aqueous protein solutions to remove virus therefrom with an ultrafiltration membrane, the membranes have a pore size sufficiently small to effect retention of the virus while permitting the protein to pass through the membrane. It is desirable that the membranes have high virus retention and at the same time high throughput. Virus retention is defined as Log Reduction Value (LRV), the number of times 10 must be multiplied to obtain the ratio of virus concentration in the feed to that in the filtrate. For example, a membrane with LRV of 4.0 means that it is capable of reducing viral load by a factor of 10,000 ($10^4$). Throughput is defined as volume of protein solution that can be passed through a given area of membrane before complete fouling occurs. As used herein, the term "complete fouling" refers to a condition of the membrane wherein less than 10% of the original flux of the membrane is observed when effecting filtration with the membrane to attain virus retention of an LRV of 3.5 or greater. It is generally observed that higher flux through the membrane and low protein binding of membrane surface both lead to higher throughput. Throughput values of a given membrane vary greatly depending on the type and concentration of protein used, pressure, ionic strength and other test conditions. Under typical process conditions, satisfactory ultrafiltration membranes have throughput of about 1000 $L/m^2$ or greater.

A more representative performance gauge of a virus retentive membrane is the membrane area that is calculated according to the $V_{max}$ method. Millipore Corporation has historically used the $V_{max}$ method for determining area requirements for normal flow filtration devices (Millipore Corporation technical note AN1025EN00). This method is based upon a gradual pore plugging model that assumes membrane plugging is a result of uniform constriction of cylindrical membrane pores. The governing equation for the model is $$t_b/V=(t_b/[V\max*A])+1/[Qi*A] \qquad (1)$$

where
 A=filtration area ($m^2$)
 V=Process Volume (L)
 $V_{max}$=Obtained from Inverse slope of a plot of t/V vs. t ($L/m^2$)=
 $Q_i$=Initial Volumetric flow rate (L/min*mhu 2)
 $t_b$=process time (min)

Equation (1) may be rearranged to estimate the filter sizing as follows:

$$A/V = 1/V\text{max} + 1/[Qi^* t_b] \qquad (2)$$

In this equation, the contribution to sizing results from both the capacity term, (1/V max) and the flow-time term (1/(Q$_i$, *t$_b$)). Most biopharmaceutical applications are intermediate plugging streams; therefore both capacity and flow rate are important in sizing. This means that both the capacity term (1/V max) and the flow-time term (1/(Q$^i$*t$_b$)) should both be used. Ignoring the flow-time term can result in significant error in determining total filtration area required. Examples of applications in which this occurs would be in bioburden reduction steps, such as prior to a column purification step, or after a depth filtration steps. In addition, many buffer and media applications are within this V$_{max}$ range. The lower the value of A, the more desirable the membrane.

In addition, when filtering an aqueous protein solution, the ultrafiltration membrane must be hydrophilic, that is readily wettable with water. A relevant method to assess hydrophilicity of a membrane is to measure the critical wetting surface tension (CWST) as described in U.S. Pat. No. 4,880,548, which is incorporated herein by reference. Briefly, the CWST of a porous medium may be determined by individually applying to its surface a series of liquids with varying surface tension, such as aqueous solution of aliphatic alcohol or inorganic salts, and observing the absorption or non-absorption of each liquid. The CWST of a porous medium, in units of dynes/cm, is defined as the mean value of the surface tension of the liquid which is absorbed and that of a liquid of neighboring surface tension which is not absorbed.

A further desirable characteristic of an ultrafiltration membrane used to filter protein solutions is that it be caustic stable since caustic solutions are commonly used for storage and sterilization of membrane prior to use.

It has been proposed in U.S. Pat. Nos. 4,794,002 and 5,139,881 to provide a porous ultrafiltration or microfiltration membrane formed of an inherently hydrophobic substrate such as a sulfone polymer substrate membrane, e.g. polysulfone or polyethersulfone, which is modified to have a hydrophilic surface as well as a process for making the membrane having the hydrophilic surface, wherein the hydrophilic surface is created by irreversible adsorption of a polymer with molecular weight of not less than 10,000. In one aspect of the invention, the surface of the substrate membrane is modified with a hydroxyalkyl cellulose such as hydroxypropylcellulose. In the process for making the membrane, the substrate membrane is contacted with the hydroxyalkylcellulose to effect adsorption onto or into the substrate membrane followed by removing excess non-adsorbed modifying hydroxylalkyl cellulose.

U.S. Pat. No. 6,214,382 discloses a hydrophilic membrane that is made by essentially the same process as in U.S. Pat. No. 4,794,002, only using a modifying polymer with number average molecular weight of 2,000 to 8,000.

U.S. Pat. No. 4,413,074 discloses a process for rendering hydrophilic a surface of a hydrophobic porous membrane such as a polysulfone. The hydrophobic membrane is contacted with a solution of hydroxyalkyl cellulose and a surfactant in a solvent such as water or a mixture of water and an aliphatic alcohol. The solvent then is removed from the membrane by heating under dry conditions to insolubilize the hydroxyalkyl cellulose.

It would be desirable to provide an ultrafiltration membrane capable of removing virus from protein solutions which has a high throughput in that high flux and low protein binding can be effected. Such a membrane would provide effective and economical virus removal from large batches of protein solution. In addition, it would be desirable to provide such a membrane which can be caustic sterilized without negatively affecting its throughput.

SUMMARY OF THE INVENTION

The present invention provides a process for adhesion of hydrophilic polymers that provides for a substantially uniform layer on the pore walls, and that thickness controlled by the thermodynamics of adhesion, rather that the stochastic nature of polymerization. The initial driving force for adhesion between a hydrophilic polymer and a hydrophobic surface is strong, but is greatly reduced after the first layer is formed, because the polymer on the surface has reduced amount of solvent associated with it, and soluble polymers do not have a thermodynamic driving force to remove solvent to adhere to such polymer. This tends to limit the layer of the hydrophilic polymer and give a substantially uniform coating on the pore walls, thus minimizing flow restriction.

The present invention also provides a hollow fiber or sheet or unilayer or multilayer, supported or unsupported ultrafiltration membrane formed of a porous membrane substrate having a modified hydrophilic surface. In one embodiment of this invention, the ultrafiltration membrane comprises a multilayer membrane having an ultrafiltration layer and at least one other layer having an average pore size larger than the average pore size of the ultrafiltration layer. This second layer provides a support for the ultrafiltration layer thereby providing it with added strength without adversely affecting the flux property of the ultrafiltration layer. The inherently hydrophobic substrate surface is rendered hydrophilic by immobilization of a hydroxyalkyl cellulose onto or into the substrate surface. The scope of this invention is not limited by a particular mechanism of immobilization of hydroxyalkyl cellulose on membrane surface. It can be immobilized by adsorption, coating, cross-linking, chemical linking to the surface or the like.

In one embodiment of this invention, the multilayer membrane is formed by cocasting two or more polymer solutions onto a support layer. The polymers for the membrane include, but are not limited to, sulfone polymers, such as polysulfone, polyethersulfone, and polyphenylsulfone. The multilayer solutions then are contacted with a nonsolvent for the polymer layers to effect coagulation and pore formation of the polymer layers thereby to effect the formation of the substrate multilayer membrane utilized in the present invention.

To render the substrate surfaces hydrophilic, the substrate multilayer membrane is contacted, such as by immersion in a solution of water, or a mixture of water with another solvent, and a hydroxylalkyl cellulose to effect immobilization of the hydroxylaklyl cellulose onto or into the substrate multilayer membrane. Excess hydroxyalkyl cellulose then is optionally removed from the substrate membrane such as by rinsing in water. The membrane then is exposed to hot water and/or steam, which can be accomplished by, for example, autoclaving, boiling, steaming, heating in an enclosed container with liquid water, or the like. It has been found that the resulting membranes having the hydrophilic surfaces autoclaved in hot water and/or steam have significantly improved flux and throughput, while maintaining high virus retention, as compared to membranes of the prior art. The hydrophilic coating that has been immobilized on the membrane in this fashion can be further chemically treated with the purpose of crosslinking, attaching specific chemical groups such as ligands for biological molecules, imparting charge to the membrane, or the like. These additional steps can be accomplished by all suitable procedures known in the art, and would include batch chemical processes, radiation-induced reactions, or the like.

The invention further embodies the use of the membranes of the present invention in a process to remove viral particles from a protein-containing solution, wherein the membrane is capable of substantially preventing the passage therethrough of virus particles and substantially permitting the passage therethrough of the protein.

DESCRIPTION OF SPECIFIC EMBODIMENTS

The hydrophobic substrate membrane utilized in the present invention can be hollow fiber or sheet or unilayer or multilayer and can be supported or unsupported.

When utilized, the hydrophobic multilayer substrate membrane in the present invention has at least one ultrafiltration layer and at least one support layer and is made by cocasting a plurality of polymer solutions, such as sulfone polymer solutions onto a support to form a multilayered liquid sheet. Thereafter, the sheet is immersed into a liquid coagulation bath to effect phase separation and form a porous ultrafiltration membrane. The pore size differences between the ultrafiltration (UF) layer and the microporous (MF) layer can differ by an order of magnitude. Also, the rate of formation of UF and MF membranes is different, with UF forming significantly faster in the coagulation bath. After formation, the porous membrane is washed free of solvent and other soluble materials. It can then be further extracted to reduce fugitive materials to a low level and then optionally be dried.

For simplicity, the process of making a multilayer cocast composite ultrafiltration membrane will be described for a two layer example. Although three or more layers may also be made by the same process. The preferred process comprises the steps of making two polymer solutions, such as two sulfone polymer solutions, one for each layer. Solutions for making porous membranes by immersion casting usually consist of a polymer, solvent and additives to modify and control the final pore size and porous nature (i.e., percent porosity, pore size distribution, etc.) of the membrane.

Suitable inherently hydrophobic substrate membranes can be formed of such polymers as sulfone polymers such as polysulforie, polyethersulfone or polyphenylsulfone, polyamides, polyimides, polyetherimide, polyethylene, polypropylene, polyvinylidene difluoroimide or blends thereof or a blend thereof with a hydrophilic polymer such as polyvinylpyrrolidone or the like.

Suitable solvents include but are not limited to dimethylsulfoxide, dimethylformamide, dimethylacetamide or N-methylpyrrolidone.

Examples of the many porogens have been used in the art, include but are not limited to compounds such as formamide, various alcohols and polyhydric compounds, water, various polyethylene glycols, polyvinyl pyrrolidone and various salts, such as calcium chloride and lithium chloride.

After the solutions are made, they are applied to a moving support carrier. For an unsupported membrane, which does not have a web attached to the final membrane, the carrier is usually a plastic film, such as polyethylene terephtalate, or a polyethylene coated paper, or similar smooth continuous web that can be easily removed from the formed multilayer membrane.

For convenience, the cocasting process for forming the porous substrate membrane will be described herein with reference to sulfone polymers. Application can be done by any standard method. The object is to coat a first sulfone polymer solution onto the carrier and a second sulfone polymer solution upon the first solution. A highly preferred method is co-casting, in which the two layers are coated with essentially no time between coatings. This can be done with a double knife over roll apparatus, or a pressurized dual slot coating head. Co-casting means that the individual layers are cast essentially simultaneously with each other with substantially no time interval between one cast layer and the next cast layer. This method is described in detail in US published Patent Application 20030217965 which is incorporated herein by reference. Co-casting allows for formation of controlled pore size regions at the junctions of layers. In the prior art, a well-defined demarcation line is formed between the sequentially cast layers. A drastic change in pore size going from a more open to a more tight structure can lead to undesirable fast accumulation of retained solute at the interface and consequently a drastic flux decline. A sharp interface can be replaced, if desired, by a more subtle change in pore size between two adjacent layers with a cocast process. Such an interfacial zone is beneficial for the retentive behavior of the overall structure of the multilayered membrane.

After the layers are cocast onto the moving carrier, the carrier with the liquid sheet is immersed into a liquid that is a nonsolvent for the polymer, and is miscible with the solvent and porogens. This will cause phase separation and the formation of a porous membrane.

The formed composite membrane is then usually separated from the carrier and washed to remove residual solvent and other material. The membrane can then be dried. Ultrafiltration membranes are usually dried with a humectant, such as glycerine, by first immersing the washed membrane in an aqueous glycerine solution, of from 5% to 25% concentration by weight, and removing excess liquid, before proceeding through the drying step. Drying is done in a manner to remove the majority of the water and to leave sufficient glycerine to prevent pore collapse.

Alternately, substrate membranes can be formulated by blending a hydrophobic polymer with a hydrophilic polymer, wherein the hydrophilic polymer remains in the final product. This is used, for example, in the case of polyethersulfone and polyvinylpyrrolidone. Membranes that are made in this fashion are usually inherently hydrophilic, however they can be further modified using the process of the present invention to impart low protein binding and other properties.

The present invention provides a caustic resistant, hollow fiber or sheet unilayered or multilayered, supported or unsupported ultrafiltration membrane having an LRV value for retaining virus of at least 4.0, preferably at least 5.0, having a hydrophilic surface and having an initial throughput of 1000 $L/m^2$ or greater, preferably 1500 $L/m^2$ or greater and which are made with the surface modified hydrophilic polymer membrane described above. The term "throughput" as used herein means the maximum volume of 1.45 g/L Bovine Serum Albumin (BSA) solution in Difko FA buffer (150 mM NaCl, pH 7.2) that can be filtered at 30 psi constant pressure at 22° C. through one square meter of the membrane. As used herein, the term "complete fouling" refers to a condition of the membrane wherein 10% or less of the original flux of the membrane is observed when effecting filtration with the membrane to attain a virus retention of initial LRV of 4.0 or greater. It should be understood that protein feeds can be highly variable, and the observed throughput can be higher or lower depending on particular protein lot and its manufacturer. However, the improvements in membrane throughput when compared to commercial membranes or membranes prepared according to the prior art, will be similar within a particular protein lot.

Other testing feeds can also be employed in throughput testing. Since one of possible applications of virus filtration membranes is purifying solutions of monoclonal antibodies, it is desirable to test hydrophilic membranes with solutions of relevant proteins, such as IgG. A commercially available solution of mixed IgGs derived from human blood serum is supplied by SeraCare Life Sciences Inc. (West Bridgewater, Mass.) and was used in a number of throughput tests on the hydrophilic membranes described in this invention. This test feed was determined to contain large aggregates of proteins and other blood components, which caused faster fouling of virus-retentive membranes by size exclusion mechanism.

The multilayer substrate membrane is surface modified by immobilizing thereon a hydroxylalkyl cellulose having the desired hydrophilicty and low protein binding. Suitable hydroxalkyl celluloses include hydroxyethyl cellulose, hydropropyl cellulose, ethyl hydroxyethyl cellulose or hydroxypropyl methyl cellulose, preferably, hydroxypropyl cellulose. Hydroxyethyl or hydropropyl are good binding groups because small molecules containing these moieties wet, and in some cases plasticize or dissolve a sulfone polymer. The hydrophobic multilayer sulfone polymer membrane is soaked in a solution of hydroxyalkyl cellulose dissolved in water or a mixture of water and an alkanol such as isopropyl alcohol. In a preferred embodiment of this invention, hydroxypropyl cellulose in water and 5 to 100 vol. %, preferably 10 to 30 vol. % isopropyl alcohol is utilized. It has been found that an increase in membrane throughput for the surface modified membrane is obtained when utilizing this solvent composition and hydroxypropyl cellulose. The time of soaking is carefully chosen, since it has to be long enough to ensure that the substrate surface is well covered, and not too long to dramatically affect flux. The preferred adsorption time is 2 to 60 minutes. Another important time consideration is manufacturability of hydrophilic membrane in a continuous fashion, which requires the soaking time to be reasonably short. U.S. Pat. No. 6,214,382 teaches that the contact time between the membrane and the modifying solution should be not less than 10 minutes, which is prohibitively long for most continuous membrane operations. In accordance with this invention, it has been determined that performing immobilization of hydroxyalkyl cellulose on the membrane surface using the conditions described herein allows shortening the time to practically 3 minutes. In a preferred embodiment of this invention, adsorption time of about 2 to 10 minutes is used. The resulting surface modified membranes can, but are not required to, then be washed with excess solvent (i.e., a modifying solution minus the modifying polymer) for preferably about 2 to 30 minutes to remove excess, noninteractive polymer. Alternately, the membrane can be dried right after soaking in the modifying polymer solution and then subjected to the heat treatment in hot water and/or steam described below. The resulting product is a membrane comprising the substrate membrane most of whose surfaces are modified by adsorption of a very thin layer of the hydroxyalkyl cellulose.

The modified multilayer membrane then can be optionally dried at room temperature. In the final process step, the surface modified membrane is then heated either by being autoclaved in the presence of water or steam such as in boiling water or in a steam atmosphere or in an autoclave at a temperature between about 40° C. and about 140° C., preferably between about 90° C. and about 122° C. or is submerged into a bath of boiling water (100° C.). It has been found that by autoclaving in the presence of water or steam, or submerging the membrane in boiling water, surface modified membranes having a significantly improved flux are obtained as compared to membranes that are not autoclaved or to membranes which are autoclaved in the absence of water or steam. It has also been found that the membranes treated in accordance with this invention has a higher Critical Wetting Surface Tension (CWST) than those obtained by simple adsorption of hydroxyalkyl cellulose such as hydroxypropyl cellulose (HPC), without autoclaving in the presence of water or steam or by being submerged in boiling water of, usually by about 3-4 dynes/cm. The data obtained on polyethersulfone films indicates that treatment of adsorbed HPC with hot steam significantly reduces dynamic water contact angles, most notably receding water contact angles (from about 30 degrees to about 9 degrees), which is a manifestation of a greater hydrophilic character.

Another indication of membrane improvement upon autoclaving in the presence of water or steam or by being submerged in boiling water is the relation between water and air flow through the membrane. Water flow is obviously measured on a wet membrane, thereby characterizing the hydrophilic coating in the hydrated, swollen state. On the other hand, air flow of dry membrane is a measure of membrane modification without taking swelling into account. Air and water fluxes of modified membranes before and after treatment with hot steam were compared. While air flow does not change significantly (suggesting that the modifying polymer is not removed to an appreciable extent), water flow improves dramatically, which indicates that the modifying polymer is now less susceptible to swelling.

| | Ratio of water flux of hydrophilized membrane to that of phobic membrane (25 psi, 20 deg. C.) | Ratio of air flow of hydrophilized membrane to that of phobic membrane (10 psi, 20 deg. C.) |
|---|---|---|
| Membrane modified with hydroxypropyl cellulose and not treated with water steam | 32.7% | 85.6% |
| Membrane modified with hydroxypropyl cellulose and treated with water steam | 48.3% | 89.8% |

Due to the increased throughput of the membranes of this invention, the filtration of protein solution to remove virus with these membranes provides significant advantages in that the membranes can be used to filter larger quantities of protein solution, and higher flux will shorten the time of filtration as compared to the membranes of the prior art.

The following examples illustrate the present invention and are not intended to limit the same.

EXAMPLE 1

A two layer polyethersulfone substrate membrane was made by cocasting two solutions of polyethersulfone in N-methylpyrrolidone followed by contacting the two layers with water to form an ultrafiltration layer and a microfiltration layer. The substrate membrane had an LRV of 4.0 for PhiX174 and water flux of 80 L/$m^2$h-psi. The substrate membrane was immersed in an aqueous solution containing 1% of hydroxypropyl cellulose and 20% isopropyl alcohol at room temperature. The membrane was soaked in this solution for 30 min, removed from solution and rinsed with deionized water for 5 min with gentle agitation. It was then placed in boiling water for 10 min and dried at room temperature. The membrane had a Critical Water Surface Tension (CWST) of 77 dynes/cm. Membrane flux was recorded to be 33.3 L/$m^2$h-psi by measuring flow of Difko FA phosphate buffer solution (150 mM NaCl, pH 7.2) at 30 psi constant pressure. The throughput was 2152 L/m² as measured with 1.45 g/L solution of BSA (Serologicals Inc., Temecula, Calif.) in the same Difko FA phosphate buffer solution that was filtered through the membrane at constant pressure of 30 psi.

COMPARATIVE EXAMPLE 1a

The procedure described in Example 1 was followed without subjecting the membrane to boiling water after modification. The membrane had a CWST of 74 dynes/cm.

COMPARATIVE EXAMPLE 1b

The procedure described in Example 1 was followed with aqueous solution containing 1% hydroxypropyl cellulose, with no alcohol deliberately added.

COMPARATIVE EXAMPLE 1c

The procedure described in Example 1 was followed with 1% solution of hydroxypropyl cellulose in isopropanol.

COMPARATIVE EXAMPLE 1d

The procedure described in Example 1 was followed with aqueous solution containing 1% hydroxypropyl cellulose, with no alcohol deliberately added. The adsorption was carried out for 16 hours, rinsed and dried at room temperature.

COMPARATIVE EXAMPLE 1e

The procedure described in Example 1 was followed with soaking time shortened to 3 minutes.

COMPARATIVE EXAMPLE 1f

The procedure described in Example 1 was followed without rinsing the membrane with cold water after soaking.

EXAMPLE 2

A two layer polyethersulfone virus-retentive substrate membrane was made by cocasting two solutions of polyethersulfone in N-methylpyrrolidone followed by contacting the two layers with water to form an ultrafiltration layer and a microfiltration layer. The substrate membrane had an LRV of 4.0 for PhiX174 and water flux of 80 L/m²h-psi. The substrate membrane was immersed in an aqueous solution containing 0.5% of hydroxypropyl cellulose, 20% isopropyl alcohol, and 0.023% surfactant Zonyl FSN (DuPont, Bridgeport, Conn.) at room temperature. The membrane was soaked in this solution for 2 min, removed from solution, excess solution was nipped off and the membrane was heated at 120 deg. C. for 15 min. Membrane flux was recorded to be 41.8 L/m²h-psi and the throughput was 1608 L/m².

EXAMPLE 3

The procedure described in Example 2 was followed. The membrane was immersed in boiling water for 5 minutes.

Table 1. Membrane flux as recorded by measuring flow of Difko FA phosphate buffer solution (150 mM NaCl, pH 7.2) at 30 psi constant pressure and throughput as measured with 1.45 g/L solution of BSA (Serologicals, Inc., Temecula, Calif.) in the same Difko FA phosphate buffer solution that was filtered through the membrane at constant pressure of 30 psi. A was calculated by Equation 2 set forth above.

|  | Flux (L/m²h-psi) | Throughput (L/m²) | Area required (m²) |
| --- | --- | --- | --- |
| Example 1 | 33.3 | 2152 | 3.6 |
| Example 1a | 22.5 | 2080 | 4.3 |
| Example 1b | 39.7 | 1190 | 5.3 |
| Example 1c | 20.8 | 1665 | 5.0 |
| Example 1d | 11.7 | 2021 | 6.0 |
| Example 1e | 38.2 | 2185 | 3.4 |
| Example 1f | 26.3 | 2232 | 3.8 |
| Example 2 | 41.8 | 1608 | 4.1 |
| Example 3 | 54.1 | 2719 | 2.6 |
| Single layer of commercial Viresolve ® NFP membrane (Millipore Corporation) | 44.9 | 475 | 11.6 |

What we claim:

1. A process for forming a virus-retentive ultrafiltration membrane having an improved flux, the process comprising the steps of:
   (a) providing a multilayer substrate membrane comprising at least one microporous layer and an ultrafiltration layer;
   (b) contacting the substrate membrane with a solution of hydroxypropyl cellulose to adsorb said hydroxypropyl cellulose onto the substrate membrane;
   (c) removing excess hydroxypropyl cellulose from the substrate membrane by rinsing in water; and
   (d) subjecting the rinsed substrate membrane to a step selected from the group consisting of: (1) autoclaving in the presence of steam or water; and (2) submerging in boiling water, thereby to form a virus-retentive ultrafiltration membrane having an improved flux relative to a membrane not subjected to step (d) subsequent to optionally rinsing in water, and further wherein the membrane has log reduction value (LRV) for Phi X174 of at least 4.0 and a throughput of 1000 L/m².

2. The process of claim 1, wherein step (d) comprises submerging the membrane substrate in boiling water.

3. The process of claim 1, wherein step (d) comprises autoclaving the membrane substrate in the presence of steam or water.

4. A process for forming a virus-retentive ultrafiltration membrane having an improved flux, the process comprising the steps of:
   (a) providing a membrane having at least one microporous layer formed from a first sulfone polymer and an ultrafiltration layer formed from a second sulfone polymer;
   (b) contacting the membrane with a solution of hydroxyalkyl cellulose to adsorb the hydroxyalkyl cellulose onto the membrane;
   (c) removing the excess hydroxyalkyl cellulose by rinsing the membrane in water; and
   (d) subjecting the rinsed membrane to a step selected from the group consisting of: (1) autoclaving in the presence of water or steam; and (2) submerging in boiling water, thereby to form a virus-retentive ultrafiltration membrane having an improved flux relative to a membrane not subjected to step (d) subsequent to optionally rinsing in water, and further wherein the membrane has log reduction value (LRV) of at least 4.0 for Phi X174 and a throughput of at least 1000 L/m².

5. The process of claim 4, wherein the hydroxyalkyl cellulose is hydroxylpropyl cellulose.

6. The process of claim 4, wherein the first sulfone polymer and the second sulfone polymer are the same sulfone polymer.

7. The process of claim 6, wherein the same sulfone polymer is polysulfone.

8. The process of claim 6, wherein the same sulfone polymer is polyethersulfone.

9. The process of claim 4, wherein either the first sulfone polymer or the second sulfone polymer is polysulfone.

10. The process of claim 4, wherein either the first sulfone polymer or the second sulfone polymer is polyethersulfone.

11. The process of claim 1, wherein the flux is improved relative to a membrane not subjected to step (d) subsequent to rinsing in water.

12. The process of claim 4, wherein the flux is improved relative to a membrane not subjected to step (d) subsequent to rinsing in water.

13. The process of claim 1, wherein the resulting membrane comprises a higher critical wetting surface tension and/or a higher throughput relative to a membrane not subjected to step (d) subsequent to rinsing in water.

14. The process of claim 4, wherein the resulting membrane comprises a higher throughput relative to a membrane not subjected to step (d) subsequent to rinsing in water.

15. The process of claim 4, wherein solution of hydroxyalkyl cellulose comprises 10-30% alkanol.

16. The process of claim 15, wherein the alkanol is isopropyl alcohol.

17. The process of claim 15, wherein the hydroxyalkyl cellulose is hydroxypropyl cellulose and the solution comprises from about 0.5 to about 1.0% hydroxypropyl cellulose.

18. The process of claim 4, wherein the membrane has a throughput of at least 1500 L/m$^2$.

19. The process of claim 4, wherein the membrane is formed by a cocasting process of first and second sulfone polymers.

20. The process of claim 4, wherein the membrane is contacted with the solution of hydroxyalkyl cellulose for about 2 to about 60 minutes.

21. A process for forming a virus-retentive ultrafiltration membrane having an improved flux, the process comprising the steps of:
   (a) providing a membrane comprising at least one microporous layer formed from a first sulfone polymer and an ultrafiltration layer formed from a second sulfone polymer, wherein the membrane is formed by a cocasting process of the first and second sulfone polymers;
   (b) contacting the membrane with a solution of hydroxyalkyl cellulose comprising 10-30% alkanol for about 2 to about 60 minutes to adsorb the hydroxyalkyl cellulose onto the membrane;
   (c) removing the excess hydroxyalkyl cellulose by rinsing the membrane in water; and
   (d) subjecting the optionally rinsed membrane to a step selected from the group consisting of:
      (1) autoclaving in the presence of water or steam; and (2) submerging in boiling water, thereby to form a virus-retentive ultrafiltration membrane having an improved flux, and further wherein the membrane has log reduction value (LRV) of at least 4.0 for Phi X174 and a throughput of at least 1500 L/m$^2$, wherein throughput is the maximum volume of 1.45 g/L Bovine Serum Albumin (BSA) solution in 150 mM NaCl, pH 7.2, that can be filtered at 30 pounds per square inch (psi) constant pressure at 22° C. through one square meter of the membrane before less than 10% of the original flux of the membrane is observed when effecting filtration with the membrane to attain virus retention of an LRV of 3.5 or greater.

\* \* \* \* \*